US011751794B2

(12) United States Patent
Deno

(10) Patent No.: US 11,751,794 B2
(45) Date of Patent: Sep. 12, 2023

(54) SYSTEM AND METHOD FOR MAPPING ELECTROPHYSIOLOGICAL ACTIVATION

(71) Applicant: St. Jude Medical, Cardiology Division, Inc., St. Paul, MN (US)

(72) Inventor: Don Curtis Deno, Andover, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 302 days.

(21) Appl. No.: 17/243,148

(22) Filed: Apr. 28, 2021

(65) Prior Publication Data

US 2021/0361215 A1 Nov. 25, 2021

Related U.S. Application Data

(60) Provisional application No. 63/026,827, filed on May 19, 2020.

(51) Int. Cl.
*A61B 5/341* (2021.01)
*A61B 5/367* (2021.01)
*A61B 5/287* (2021.01)

(52) U.S. Cl.
CPC .............. *A61B 5/341* (2021.01); *A61B 5/367* (2021.01); *A61B 5/287* (2021.01)

(58) Field of Classification Search
None
See application file for complete search history.

(56) References Cited

U.S. PATENT DOCUMENTS 4,649,924 A 3/1987 Taccardi
5,297,549 A 3/1994 Beatty et al.
(Continued)

FOREIGN PATENT DOCUMENTS

EP 1166714 1/2002
EP 1336379 8/2003
(Continued)

OTHER PUBLICATIONS

Magtibay et al., "Reinserting Physiology into Cardiac Mapping Using Omnipolar Electrograms," Sep. 2019, Cardiac Electrophysiology Clinics, vol. 11, Issue 3, pp. 525-536. (Year: 2019).*
(Continued)

*Primary Examiner* — Kennedy Schaetzle
(74) *Attorney, Agent, or Firm* — Wiley Rein

(57) ABSTRACT

Electrical activation of tissue can be mapped from using electrophysiological data from a plurality of electrodes carried by a high density grid catheter. Each clique of three or more electrodes will define a pair of orthogonal bipoles as well as several unipoles. An electroanatomical mapping system can analyze the electrophysiological data such that, for each clique, an integral of an omnipolar electrogram the best morphologically matches a representative (e.g., average) unipolar electrogram for the clique is identified. The orientation of the best-fit omnipole is then defined as the activation direction for the clique. The conduction velocity magnitude can also be computed as a ratio of an amplitude of the unipolar electrogram for the clique to an amplitude of the integral of the omnipolar electrogram for the clique along the activation direction. The resulting activation map can also be output graphically.

20 Claims, 7 Drawing Sheets

(56) References Cited

U.S. PATENT DOCUMENTS

| | | | |
|---|---|---|---|
| 5,546,270 A | 8/1996 | Konno et al. | |
| 5,697,377 A | 12/1997 | Wittkampf | |
| 5,848,972 A | 12/1998 | Triedman et al. | |
| 5,921,923 A | 7/1999 | Kuck et al. | |
| 5,983,126 A | 11/1999 | Wittkampf | |
| 6,233,476 B1 | 5/2001 | Strommer et al. | |
| 6,360,121 B1 | 3/2002 | Shoda et al. | |
| 6,400,981 B1 | 6/2002 | Govari | |
| 6,498,944 B1 | 12/2002 | Ben-Haim et al. | |
| 6,640,119 B1 | 10/2003 | Budd et al. | |
| 6,690,963 B2 | 2/2004 | Ben-Haim et al. | |
| 6,728,562 B1 | 4/2004 | Budd et al. | |
| 6,788,967 B2 | 9/2004 | Ben-Haim et al. | |
| 6,939,309 B1 | 9/2005 | Beatty et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |
| 7,197,354 B2 | 3/2007 | Sobe | |
| 7,263,397 B2 | 8/2007 | Hauck et al. | |
| 7,386,339 B2 | 6/2008 | Strommer et al. | |
| 7,885,707 B2 | 2/2011 | Houck | |
| 8,862,213 B2 | 10/2014 | Lo et al. | |
| 8,876,817 B2 | 11/2014 | Avitall et al. | |
| 2006/0253030 A1 | 11/2006 | Altmann et al. | |
| 2007/0225589 A1 | 9/2007 | Viswanathan | |
| 2008/0183088 A1 | 7/2008 | Lian et al. | |
| 2008/0221643 A1 | 9/2008 | Olson | |
| 2009/0248014 A1 | 10/2009 | Shachar et al. | |
| 2010/0168557 A1 | 7/2010 | Deno et al. | |
| 2010/0168560 A1 | 7/2010 | Hauck et al. | |
| 2013/0190747 A1 | 7/2013 | Avitall et al. | |
| 2013/0274582 A1 | 10/2013 | Afonso et al. | |
| 2013/0345537 A1 | 12/2013 | Thakur et al. | |
| 2014/0058375 A1 | 2/2014 | Koblish | |
| 2014/0200430 A1 | 7/2014 | Spector | |
| 2014/0235996 A1 | 8/2014 | Kim et al. | |
| 2014/0336518 A1 | 11/2014 | Shuros et al. | |
| 2014/0343442 A1 | 11/2014 | Thakur et al. | |
| 2016/0045133 A1 | 2/2016 | Balachandran et al. | |
| 2016/0331471 A1 | 11/2016 | Deno et al. | |
| 2017/0042449 A1 | 2/2017 | Deno et al. | |
| 2017/0049348 A1 | 2/2017 | Deno et al. | |
| 2018/0279896 A1* | 10/2018 | Ruppersberg ...... | A61B 18/1492 |
| 2018/0296111 A1 | 10/2018 | Deno et al. | |

FOREIGN PATENT DOCUMENTS

| | | |
|---|---|---|
| EP | 2186474 | 5/2010 |
| JP | 11047148 | 2/1999 |
| JP | 2001-061789 | 3/2001 |
| JP | 2002-051998 | 2/2002 |
| JP | 2007537831 | 12/2007 |
| JP | 2012524606 | 10/2012 |
| JP | 2016-518224 | 6/2016 |
| WO | 1997/024983 | 7/1997 |
| WO | 2012/037471 | 3/2012 |
| WO | 2012-092016 | 7/2012 |
| WO | 2014/113612 | 7/2014 |
| WO | 2014/182822 | 11/2014 |
| WO | 2015/130824 | 9/2015 |
| WO | 2016/183247 | 11/2016 |

OTHER PUBLICATIONS

International Search Report and Written Opinion for International Application No. PCT/US2018/027607, dated Sep. 12, 2018, 16 pages.

Mazeh et al., "A Simplified Approach for Simultaneous Measurements of Wavefront Velocity and Curvature in the Heart Using Activation Times", Cardiovascular Engineering and Technology, 4:4 (Dec. 2013), pp. 520-534.

Michaud et al., "Information at our Catheter Tips: Unipolar Electrogram Morphology Makes Another Comback!", Heart Rhythm, 7:9 (Sep. 2010), pp. 1301-1302.

Mironov et al., "Role of Conduction Velocity Restitution and Short-Term Memory in the Development of Action Potential Duration Alternans in Isolated Rabbit Hearts", Circulation (Jul. 1, 2008), pp. 17-25.

Mountantonakis et al., "Relationship between Voltage Map 'Channels' and the Location of Critical Isthmus Sites in Patients wrth Post-Infarction Cardiomyopathy and Ventricular Tanycardia", JACC 61:20 (May 21, 2013), pp. 2088-2095.

Nanthakumar et al., "Regional Differences in Ventricular Fibrillation in the Open-Chest Porcine Left Ventricle", Circulation Research (Oct. 18, 2002), pp. 733-740.

Narayan et al., "Treatment of Atrial Fibrillation by the Ablation of Localized Sources", JACC 60:7 (Aug. 14, 2012), pp. 628-636.

Nayyar et al., "High-Density Mapping of Ventricular Scar A Comparison of Ventricular Tachycardia (VT) Supporting Channels with Channels that do not Support VT", Circulation (Feb. 2014), pp. 90-98.

Otomo et al., "Local Unipolar and Bipolar Electrogram Criteria for Evaluating the Transmurality of Atrial Ablation Lesions at Different Catheter Orientations Relative to the Endocardial Surface", Heart Rhythm 7:9 (Sep. 2010), pp. 1291-1300.

Parson et al., "Cardiac Mapping Instrumentation for the Instantaneous Display of Endocardial and Epicardial Activation", IEEE Transactions on Biomedical Engineering, vol. BME-34, No. 6 (Jun. 1987), pp. 468-472.

Patel et al., "Electroanatomic Mapping of the Intercaval Bundle in Atrial Fibrillation", Circulation (Dec. 2014), pp. 1262-1267.

Pieper et al., "Simultaneously Collected Monopolar and Discrete Bipolar Electrograms: Comparison of Activation Time Detection Algorithms", PACE, vol. 16 (Mar. 1993), pp. 426-433.

Plank et al., "Cardiac Near-Field Morphology During Conduction Around a Microscopic Obstacle—a Computer Simulation Study", Annals of Biomedical Engineering, 31:10 (Nov. 2003), pp. 1206-1212.

Plank et al., "Model Study of Vector-Loop Morphology During Electrical Mapping of Microscopic Conduction in Cardiac Tissue", Annals of Biomedical Engineering, 28:10 (Oct. 2000), pp. 1244-1252.

Plank et al., "Use of Cardiac Electric Near-Field Measurements to Determine Activation Times", Annals of Biomedical Engineering, 31:9 (Oct. 2003), pp. 1066-1076.

Price et al., "Novel Ablation Catheter Technology that Improves Mapping Resolution and Monitoring of Lesion Maturation", The Journal of Innovations in Cardiac Rhythm Management, (Jan. 2012), pp. 599-609.

Ravelli et al., "Wave Similarity Mapping Shows the Spatiotemporal Distribution of Fibrillatory Wave Complexity in the Human Right Atrium During Paroxysmal and Chronic Atrial Fibrillation", Journal of Cardiovascular Electrophysiology, 16:10 (Oct. 2005), pp. 1071-1076.

Rogers et al., "Quantitative Techniques for Analyzing High-Resolution Cardiac-Mapping Data", IEEE Engineering in Medicine and Biology, 17:1 (Jan./Feb. 1998), pp. 62-72.

Schilling et al., "Simultaneous Endocardial Mapping in the Human Left Ventricle Using a Noncontact Catheter Comparison of Contact and Reconstructed Electropgrams During Sinus Rhythm", Circulation (Sep. 1, 1998), pp. 887-898.

Schmitt et al., "Symposium on Electrocardiography and Vectorcardiography the Present Status of Vectorcardiography", JAMA Internal Medicine 96:5 (Nov. 1955), pp. 574-590.

Schuler et al., "Influence of Catheter Orientation, Tissue Thickness and Conduction Velocity on the Intracardiac Electrogram", Biomed Tech 2013; 58 (Suppl. 1), 2 pages.

Schumacher et al., "Transverse Conduction Capabilities of the Crista Terminalis in Patients with Atrial Flutter and Atrial Fibrillation", JACC 34:2 (Aug. 1999), pp. 363-373.

Shors et al., "A Method for Determining High-Resolution Activation Time Delays in Unipolar Cardiac Mapping"; IEEE Transactions on Biomedical Engineering, 43:12 (Dec. 1996), pp. 1192-1196.

(56) References Cited

OTHER PUBLICATIONS

Spears et al., "Relationship of Bipolar and Unipolar Electrogram Voltage to Scar Transmurality and Composition Derived by Magnetic Resonance Imaging in Patients with Nonischemic Cardiomyopathy Undergoing VT Ablation", Heart Rhythm 9:11 (Nov. 2012), pp. 1837-1846.
Stevenson et al., "Recording Techniques for Clinical Electrophysiology", Journal of Cardiovascular Electrophysiology 16:9 (Sep. 2005), pp. 1017-1022.
Tedrow et al., "Recording and Interpreting Unipolar Electrograms to Guide Catheter Ablation", Heart Rhythm 8:5 (May 2011), pp. 791-796.
Thompson et al., "Improved Spatial Resolution and Electrogram Wave Direction Independence with the Use of an Orthogonal Electrode Configuration", J Clin Monit Comput 28: (Apr. 2014), pp. 157-163.
Tungjikusolmun et al., "Guidelines for Predicting Lesion Size at Common Endocardial Locations During Radio-Frequency Ablation", IEEE Transactions on Biomedical Engineering 48:2 (Feb. 2001), pp. 194-201.
Weber et al., "Conduction Velocity Restitution of the Human Atrium—An Efficient Measurement Protocol for Clinical Electrophysiological Studies", IEEE Transactions on Biomedical Engineering, 58:9 (Sep. 2011), pp. 2648-2655.
Weber et al., "Wave-Direction and Conduction-Velocity Analysis from Intracardiac Electrograms—A Single-Shot Technique", IEEE Transactions on Biomedical Engineering, 57:10 (Oct. 2010), pp. 2394-2401.
Wilkowski et al., "In Vivo Estimation of Cardiac Transmembrane Current", Circulation Research 72:2 (Feb. 1993), pp. 424-439.
Yamada, "Pulmonary Vein Isolation with a Multielectrode Basket Cather", Indian Pacing and Electrophysiology Journal, 7(2) (2006), pp. 97-109.
Zaman et al., "The Rotor Revolution Conduction at the Eye of the Storm in Atrial Fibrillation", Circulation (Dec. 2014), pp. 1230-1236.
Zhang et al., "Noninvasive Three-Dimensional Electrocardiographic Imaging of Ventricular Activation Sequence", Am J Physiol Heart Circ Physiol, vol. 289 (Aug. 5, 2005), pp. H2724-H2732.
Yamada et al., "Electrophysiological Pulmonary Vein Antrum Isolation with a Multielectrode Basket Catheter is Feasible and Effective for Curing Paroxysmal Atrial Fibrillation: Efficacy of Minimally Extensive Pulmonary Vein Isolation", Heart Rhythm, 3:4 (Apr. 2006), pp. 377-384.
Anter et al., "High-Resolution Mapping of Scar-Related Atrial Arrhythmias Using Smaller Electrodes with Closer Interelectrode Spacing", Circulation 8:3 (Jun. 2015), 31 pages.
Arora et al., "Fundamentals of Intracardiac Mapping", Catheter Ablation of Cardia Arrhythmias (2006), pp. 107-134.
Avitall et al., "Maximal Electrogram Attenuation recorded from Mini Electrodes Embedded on 4.5-mm irrigated and 8-mm Nonirrigated Catheters Signifies Lesion Maturation", Journal of Cardiovascular Electrophysiology 26:2 (Feb. 2015), pp. 1-11.
Balasundaram et al., "Tracking Rotors with Minimal Electrodes: Modulation Index Based Strategy", Circulation 8:2 (Apr. 2015), 34 pages.
Barnette et al., "Estimation of a 3-D Conduction Velocity Vector Fields from Cardiac Mapping Data", Computers in Cardiology, vol. 25 (Sep. 1998), pp. 605-608.
Bayly et al., "Estimation of Conduction Velocity Vector Fields from Epicardial Mapping Data", IEEE Transactions on Biomedical Engineering, 45:5 (May 1998), pp. 563-571.
Bayly et al., "Estimatation of Conduction Velocity Vector Fields from 504-Channel Epicardial Mapping Data", Computers in Cardiology (Sep. 1996), pp. 133-136.
Chan et al., "The Effect of Ablation Length and Catheter Tip to Endocardial Orientation on Radiofrequency Lesion Size in the Canine Right Atrium", PACE 25:1 (Jan. 2002), pp. 4-13.
Damle et al., "Atrial and Accessory Pathway Activation Direction in Patients with Orthodromic Supraventricular Tachycardia: Insights from Vector Mapping", JACC 23:3 (Mar. 1, 1994), pp. 684-692.
de Bakker et al., "The Pathophysiologic Basis of Fractionated and Complex Electrograms and the Impact of Recording Techniques on Their Detection and Interpretation", Circulation (Apr. 2010), 3: pp. 204-213.
de Bakker et al., "Activation Mapping: Unipolar Versus Bipolar Recording", Cardiac Electrophysiology—From Cell to Bedside—Second Edition ISBN 0-7216-4941-6, pp. 1068-1078.
Deng et al., Simulation of Biatrial Conduction via Different Pathways during Sinus Rhythm with a Detailed Human Atrial Model, Journal of Zhjiang University—Science B (Biomedicine & Biotechnology), Sep. 2012, 13(9): pp. 676-694.
Deng et al., "An Image-Based Model of the Whole Human Heart with Detailed Anatomical Structure and Fiber Orientation", Computational and Mathematical Methods in Medicine, vol. 2012; Jul. 2012, 16 pages.
Desai et al., "Two Phase Radiofrequency Catheter Ablation of Isolated Ventricular Endomyocardium", PACE vol. 14, (Jul. 1991), pp. 1179-1194.
Dubois et al., "Global and Directional Activation Maps for Cardiac Mapping in Electrophysiology", Computing in Cardiology (Sep. 2012), 39: pp. 349-352.
Faes et al., "A Method for Quantifying Atrial Fibrillation Organization Based on Wave-Morphology Similarity", IEEE Transactions on Biomedical Engineering, 49:12 (Dec. 2002), pp. 1504-1513.
Fedotov et al., "Methods for Increasing the Reliability of Coordinate Determination by the Location and Imaging Systems of Endocardial Electrodes", Biomedical Engineering 41:4 (Jul. 2007), pp. 145-149.
Fisher et al., "Three-Dimensional Electrogram Mappping Improves Ablation of Left-Sided Accessory Pathways", PACE, vol. 15 (Dec. 1992), pp. 2344-2356.
Fitzgerald et al., "Comparative Psychometric Analysis of Vector and Isochrone Cardiac Activation Maps", IEEE Transactions on Biomedical Engineering 51:5 (May 2004), pp. 847-855.
Fitzgerald et al., "Estimation of Cardiac Conduction Velocities Using Small Data Sets", Annals of Biomedical Engineering, vol. 31 (Mar. 2003), pp. 250-261.
Fitzgerald et al., "Identification of Cardiac Rhythm Features by Mathematical Analysis of Vector Fields", IEEE Transactions on Biomedical Engineering 52:1 (Jan. 2005), pp. 19-29.
Gaudette et al., "Epicardial Velocity Estimation Using Wavelets", Computers in Cardiology 24 (Sep. 1997), pp. 339-342.
Gerstenfeld et al., "Detection of Changes in Atrial Endocardial Activation with Use of an Orthogonal Catheter", JACC 18:4 (Oct. 1991), pp. 1034-1042.
Gerstenfeld et al., "Evidence for Transient Linking of Atrial Excitation During Atrial Fibrillation in Humans", Circulation 86:2 (Aug. 1992), pp. 375-382.
Gornick et al., "Validation of a New Noncontact Catheter System for Electroanatomic Mapping of Left Ventricular Endocardium", Circulation (1999), 99: 829-835.
Gupta et al., "Rapid Ablation of Recurrent Atrial Flutter Using a Novel Ablation Catheter", The Journal of Innovations in Cardiac Rhythm Management (Nov. 2014), No. 5, pp. 1808-1812.
Haddad et al., "Novel Algorithmic Methods in Mapping of Atrial and Ventricular Tachycardia", Circulation (Jun. 2011), 29 pages.
Harrild et al., "A Computer Model of Normal Conduction in the Human Atria", Circulation Research (Sep. 29, 2000), 12 pages.
Horner et al., "Electrode for Recording Direction of Activation, Conduction Velocity, and Monophasic Action Potential of Myocardium", The American Physiological Society (Apr. 1997), pp. H1917-H1927.
Huang et al., "Evolution ofthe Organization of Epicardial Activation Patterns During Ventricular Fibrillation", Journal of Cardiovascular Electrophysiology (Dec. 1998), 9:12, pp. 1291-1304.
Ideker et al., "The Assumptions of Isochronal Cardiac Mapping", PACE, vol. 12 (Mar. 1989), pp. 456-478.
Irie et al., "Relationship Between Sinus Rhythm Late Activation Zones and Critical Sites for Scar-Related Ventricular Tachycardia: A Systematic Analysis of Isochronal Late Activation Mapping", Circulation (Apr. 2015), 32 pages.

(56) References Cited

OTHER PUBLICATIONS

Kadish et al., "Vector Mapping Myocardial Activation", Circulation (Sep. 1986), 74:3, pp. 603-615.
Karney et al., "Quaternions in Molecular Modeling", Journal of Molecular Graphics and Modeling 25 (Jan. 2007), pp. 595-604.
Kay et al., "Measuring Curvature and Velocity Vector Fields for Waves of Cardiac Excitation in 2-D Media", IEEE Transactions on Biomedical Engineering 52:1 (Jan. 2005), pp. 50-63.
Kearsley, "On the Orthogonal Transformation Used for Structural Comparisons", Acta Cryst (Feb. 1, 1989), Section A45, pp. 208-210.
Kumar et al., "Unipolar Electrogram Morphology to Assess Lesion Formation During Catheter Ablation of Atrial Fibrillation Successful Translation into Clinical Practice", Circulation (Dec. 2013), pp. 1050-1052.
Lindsay et al., "Novel Directional Activation Map Using Local Propagation Between Adjacent Electrograms", Heart Rhythm 8:5 (May Supplement 2011), 2 pages.
Liu et al., "Three-Dimensional Imaging of Ventricular Activation and Electrograms from Intracavitary Recordings", IEEE Transactions on Biomedical Engineering 58:4 (Apr. 2011), pp. 868-875.
Liu et al., "Functional Characterization of the Crista Terminalis in Patients with Atrial Flutter: Implications of Radiofrequency Ablation", JACC 43:9 (May 5, 2004), pp. 1639-1645.
Mase et al., "Velocity Field Analysis of Activation Maps in Atrial Fibrillation a Simulation Study", World Congress (Sep. 2009), IFMBE Proceedings 25/IV, pp. 1014-1017.
Kadish et al., "Mapping of Atrial Activation with a Noncontact, Multielectrode Catheter in Dogs", Circulation (1999), 99: pp. 1906-1913.
Benharash, "Quantitative Analysis of Localized Sources Identified by Focal Impulse and Rotor Modulation Mapping in Atrial Fibrillation", Circulation (Jun. 2015), pp. 554-561.
Bharati et al., "The Conduction System of the Swine Heart", Chest 100:1 (Jul. 1991), pp. 207-212.
Bortone et al., "Unipolar Signal Modification as a Guide for Lesion Creation During Radiofrequency Application in the Left Atrium Prospective Study in Humans in the Setting of Paroxysmal Atrial Fibrillation Catheter Ablation", Circulation (Dec. 2013), pp. 1095-1102.
Bouman et al., "Structure and Function of the Sino-Atrial Node: A Review", European Heart Journal 7:2 (Feb. 1986), pp. 94-104.
Boyett et al., "The Sinoatrial Node, a Heterogeneous Pacemaker Structure", Cardiovascular Research 47:4 (2000), pp. 658-687.
Burch et al., "Chapter X The Development of Spatial Vectrocardiography", A History of Electrocardiography, Norman Publishing (Apr. 1990), pp. 235-248.
Cantwell et al., "Techniques for Automated Local Activation Time Annotation and Conduction Velocity Estimation in Cardiac Mapping", Computers in Biology and Medicine (Oct. 1, 2015), pp. 1-14.
Casella et al., "Feasibility of Combined Unipolar and Bipolar Voltage Maps to Improve Sensitivity of Endomycardial Biopsy", Circulation (Jun. 2015), 36 pages.
International Search Report and Written Opionion of the International Searching Authority dated Aug. 4, 2021.
Don C. Deno, et al.; "High-resolution, live, directional mapping"; Heart Ryhthm, [Online]; vol. 17, No. 9; May 10, 2020.

* cited by examiner

1000

SYSTEM AND METHOD FOR MAPPING ELECTROPHYSIOLOGICAL ACTIVATION

CROSS-REFERENCE TO RELATED APPLICATIONS

The instant application claims the benefit of U.S. provisional application No. 63/026,827, file 19 May 2020, which is hereby incorporated by reference as though fully set forth herein.

BACKGROUND

The present disclosure relates generally to electrophysiological mapping, such as may be performed in cardiac diagnostic and therapeutic procedures. In particular, the present disclosure relates to systems, apparatuses, and methods for mapping and visualizing electrophysiological tissue activation, including the use of data collected by a high density ("HD") grid catheter or other multi-electrode device.

Electrophysiological mapping, and more particularly electrocardiographic mapping, is a part of numerous cardiac diagnostic and therapeutic procedures. These studies often include mapping the activation wavefront as it propagates along the cardiac surface, because visualizations of activation maps can provide insight to a practitioner as to how an arrythmia is traveling through the cardiac chambers and where it might be treated.

BRIEF SUMMARY

The instant disclosure provides a method of mapping cardiac activation, including the steps of: receiving, at an electroanatomical mapping system, electrophysiological data from a plurality of electrodes carried by a multi-electrode catheter, the plurality of electrodes defining a plurality of cliques; and for each clique of the plurality of cliques, the electroanatomical mapping system executing a process including: identifying an integral of an omnipolar electrogram for the clique having a best morphological match to a unipolar electrogram for the clique; defining an orientation of the omnipolar electrogram for the clique having the best morphological match to the unipolar electrogram for the clique as an activation direction for the clique; and computing a conduction velocity magnitude for the clique using the integral of the omnipolar electrogram for the clique and the unipolar electrogram for the clique, thereby determining a cardiac activation map.

The unipolar electrogram for the clique can be a representative unipolar electrogram for the clique, such as an average unipolar electrogram for the clique.

The step of computing a conduction velocity magnitude for the clique using the integral of the omnipolar electrogram for the clique and the unipolar electrogram for the clique can include computing the conduction velocity magnitude for the clique as a ratio of an amplitude of the unipolar electrogram for the clique to an amplitude of the integral of the omnipolar electrogram along the activation direction for the clique.

The integral of the omnipolar electrogram for the clique can be an integral of the omnipolar electrogram for the clique with respect to time.

The method can also include outputting a graphical representation of the cardiac activation map.

According to aspects of the disclosure, the multi-electrode catheter can be a high density grid catheter.

In additional aspects of the disclosure, each clique of the plurality of cliques includes three electrodes that define two orthogonal bipoles.

Also disclosed herein is an electroanatomical mapping system for generating a cardiac activation map. The system includes an activation mapping and visualization processor configured to: receive electrophysiological data from a plurality of electrodes carried by a multi-electrode catheter, the plurality of electrodes defining a plurality of cliques; and for each clique of the plurality of cliques, determine an activation direction and conduction velocity magnitude according to a process including: identifying an integral of an omnipolar electrogram for the clique having a best morphological match to a unipolar electrogram for the clique; defining an orientation of the omnipolar electrogram for the clique having the best morphological match to the unipolar electrogram for the clique as an activation direction for the clique; and computing a conduction velocity magnitude for the clique using the integral of the omnipolar electrogram for the clique and the unipolar electrogram for the clique, thereby determining a cardiac activation map.

The activation mapping and visualization processor can further be configured to output a graphical representation of the activation map.

It is contemplated that the unipolar electrogram for the clique can be a representative unipolar electrogram for the clique, such as an average unipolar electrogram for the clique.

The electroanatomical mapping system can compute the conduction velocity magnitude for the clique using the integral of the omnipolar electrogram for the clique and the unipolar electrogram for the clique by computing the conduction velocity magnitude for the clique as a ratio of an amplitude of the unipolar electrogram for the clique to an amplitude of the integral of the omnipolar electrogram for the clique.

The integral of the omnipolar electrogram for the clique can be an integral of the omnipolar electrogram for the clique with respect to time.

The instant disclosure also provides a method of mapping electrical activation of tissue. The method includes: receiving, at an electroanatomical mapping system, electrophysiological data from a plurality of electrodes carried by a high density grid catheter, the plurality of electrodes defining a plurality of cliques, each clique including three electrodes that define a pair of orthogonal bipoles; and for each clique of the plurality of cliques, the electroanatomical mapping system executing a process including: identifying an integral of an omnipolar electrogram for the clique having a best morphological match to a unipolar electrogram for the clique; defining an orientation of the omnipolar electrogram for the clique having the best morphological match to the unipolar electrogram for the clique as an activation direction for the clique; and computing a conduction velocity magnitude for the clique using the integral of the omnipolar electrogram for the clique and the unipolar electrogram for the clique, thereby determining an activation map for the tissue.

The unipolar electrogram for the clique can be a representative unipolar electrogram for the clique, such as an average unipolar electrogram for the clique.

The step of computing a conduction velocity magnitude for the clique using the integral of the omnipolar electrogram for the clique and the unipolar electrogram for the clique can include computing the conduction velocity magnitude for the clique as a ratio of an amplitude of the unipolar electrogram for the clique to an amplitude of the integral of the omnipolar electrogram for the clique.

The integral of the omnipolar electrogram for the clique can be an integral of the omnipolar electrogram for the clique with respect to time.

The method can further include outputting a graphical representation of the activation map for the tissue.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides systems, apparatuses, and methods for generating and visualizing electrophysiology maps, and in particular maps of electrophysiological activation of tissue. For purposes of illustration, aspects of the disclosure will be described with reference to cardiac activation maps, created from intracardiac electrograms collected using a high density (HD) grid catheter, such as the Advisor™ HD grid mapping catheter from Abbott Laboratories (Abbott Park, Ill.), in conjunction with an electroanatomical mapping system, such as the EnSite Precision™ cardiac mapping system, also from Abbott Laboratories. Those of ordinary skill in the art will understand, however, how to apply the teachings herein to good advantage in other contexts and/or with respect to other devices.

Figure 1:
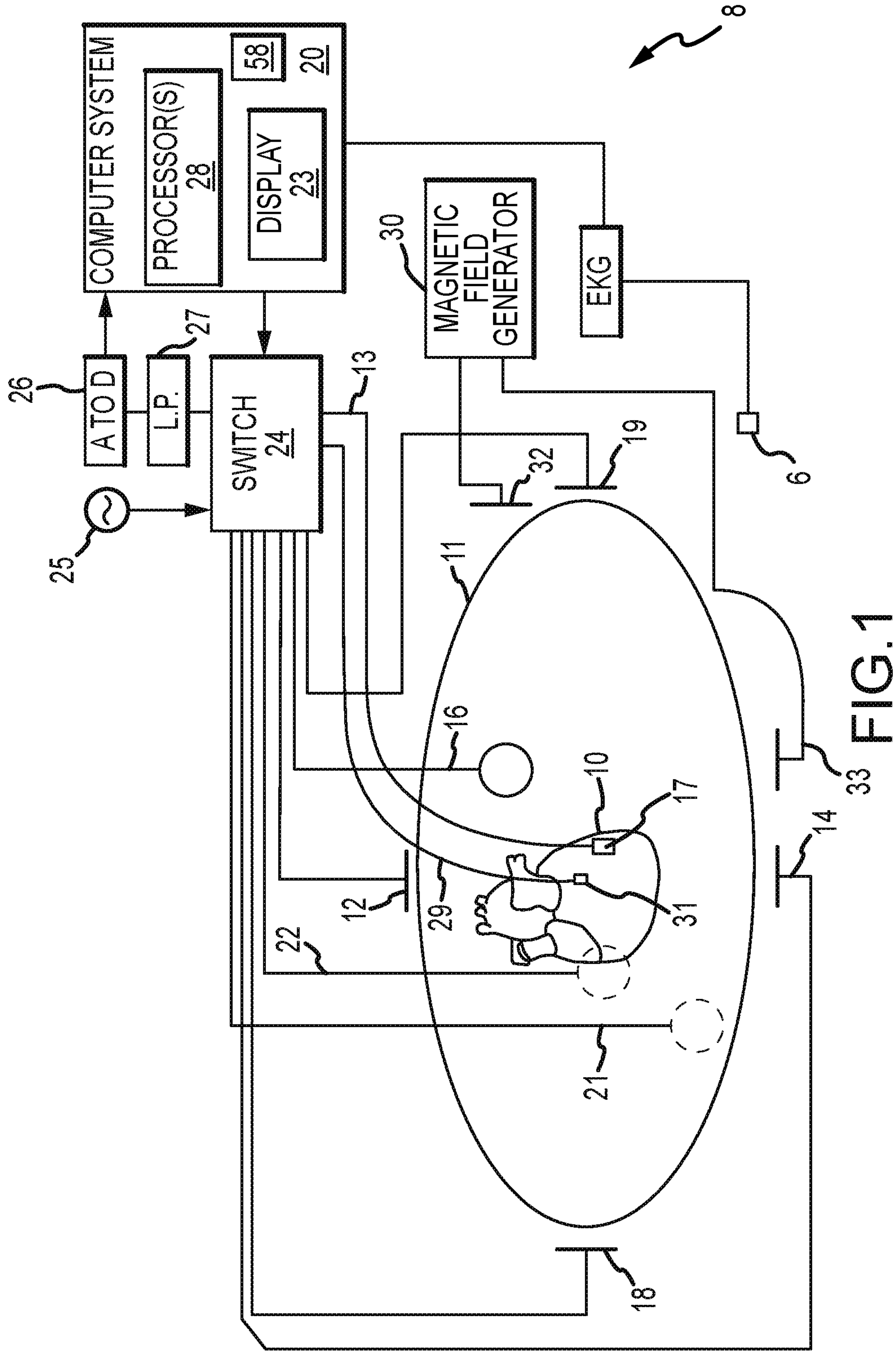
FIG. 1 is a schematic diagram of an exemplary electroanatomical mapping system.

FIG. 1 shows a schematic diagram of an exemplary electroanatomical mapping system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, system 8 determines the location, and in some aspects the orientation, of objects, typically within a three-dimensional space, and expresses those locations as position information determined relative to at least one reference. This is referred to herein as "localization."

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only a single lead 6 and its connection to computer 20 is illustrated in FIG. 1.

A representative catheter 13 having at least one electrode 17 is also shown. This representative catheter electrode 17 is referred to as the "roving electrode," "moving electrode," or "measurement electrode" throughout the specification. Typically, multiple electrodes 17 on catheter 13, or on multiple such catheters, will be used. In one embodiment, for example, the system 8 may comprise sixty-four electrodes on twelve catheters disposed within the heart and/or vasculature of the patient. In other embodiments, system 8 may utilize a single catheter that includes multiple (e.g., eight) splines, each of which in turn includes multiple (e.g., eight) electrodes.

Figure 2:
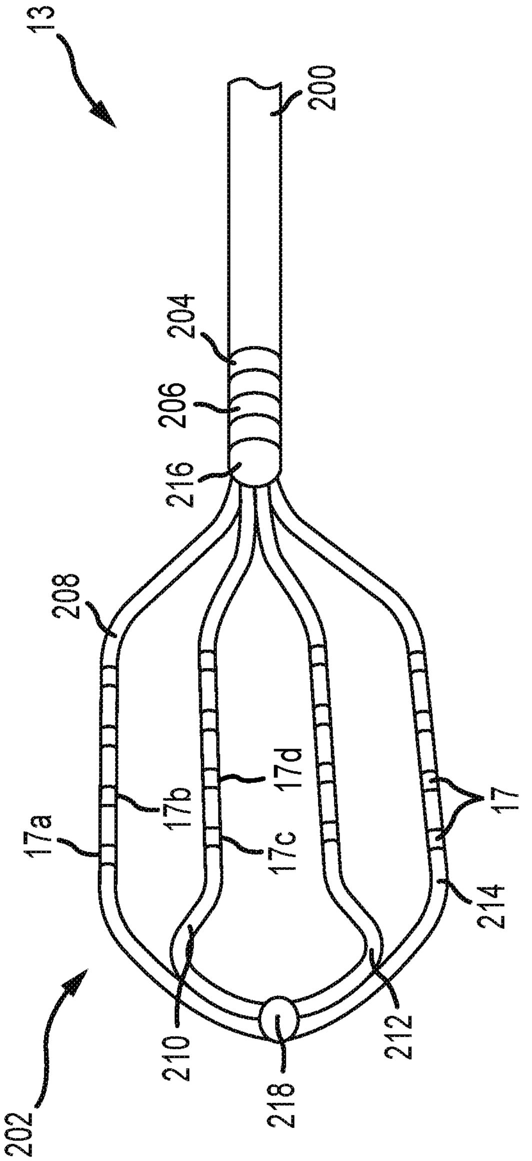
FIG. 2 depicts an exemplary catheter that can be used in connection with aspects of the instant disclosure.

The foregoing embodiments are merely exemplary, however, and any number of electrodes and/or catheters may be used. For example, for purposes of this disclosure, a segment of an exemplary multi-electrode catheter, and in particular an HD grid catheter 13 such as the Advisor™ HD Grid Mapping Catheter, Sensor Enabled™ (Abbott Laboratories, Abbott Park, Ill.), is shown in FIG. 2. HD grid catheter 13 includes a catheter body 200 coupled to a paddle 202. Catheter body 200 can further include first and second body electrodes 204, 206, respectively. Paddle 202 can include a first spline 208, a second spline 210, a third spline 212, and a fourth spline 214, which are coupled to catheter body 200 by a proximal coupler 216 and to each other by a distal coupler 218. In one embodiment, first spline 208 and fourth spline 214 can be one continuous segment and second spline 210 and third spline 212 can be another continuous segment. In other embodiments, the various splines 208, 210, 212, 214 can be separate segments coupled to each other (e.g., by proximal and distal couplers 216, 218, respectively). It should be understood that HD catheter 13 can include any number of splines; the four-spline arrangement shown in FIG. 2 is merely exemplary.

As described above, splines 208, 210, 212, 214 can include any number of electrodes 17; in FIG. 2, sixteen electrodes 17 are shown arranged in a four-by-four array. It should also be understood that electrodes 17 can be evenly and/or unevenly spaced, as measured both along and between splines 208, 210, 212, 214. For purposes of easy reference in this description, FIG. 3A provides alphanumeric labels for electrodes 17.

As those of ordinary skill in the art will recognize, any two neighboring electrodes 17 define a bipole. Thus, the 16 electrodes 17 on catheter 13 define a total of 42 bipoles—12 along splines (e.g., between electrodes 17*a* and 17*b*, or between electrodes 17*c* and 17*d*), 12 across splines (e.g., between electrodes 17*a* and 17*c*, or between electrodes 17*b* and 17*d*), and 18 diagonally between splines (e.g., between electrodes 17*a* and 17*d*, or between electrodes 17*b* and 17*c*).

Figure 3B:
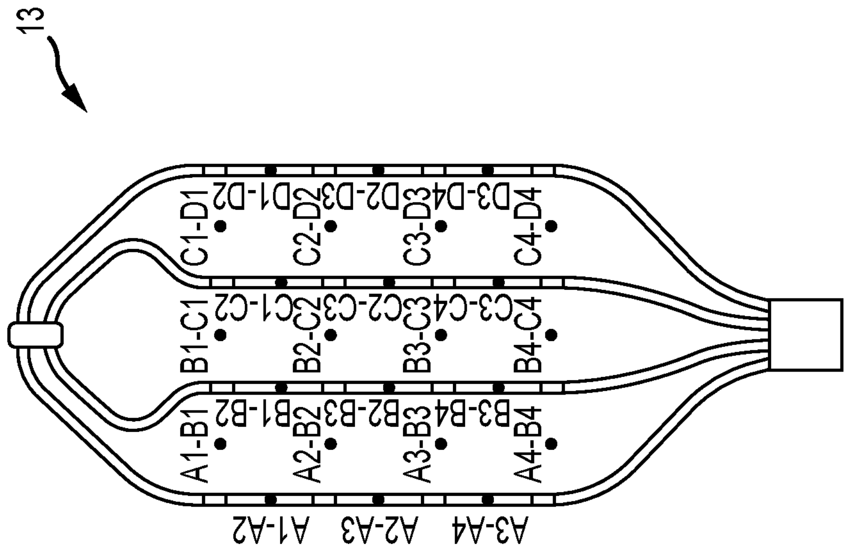
FIGS. 3A and 3B provide alphanumeric labeling conventions for electrodes carried by a multi-electrode catheter and the bipoles associated therewith.
Figure 3A:
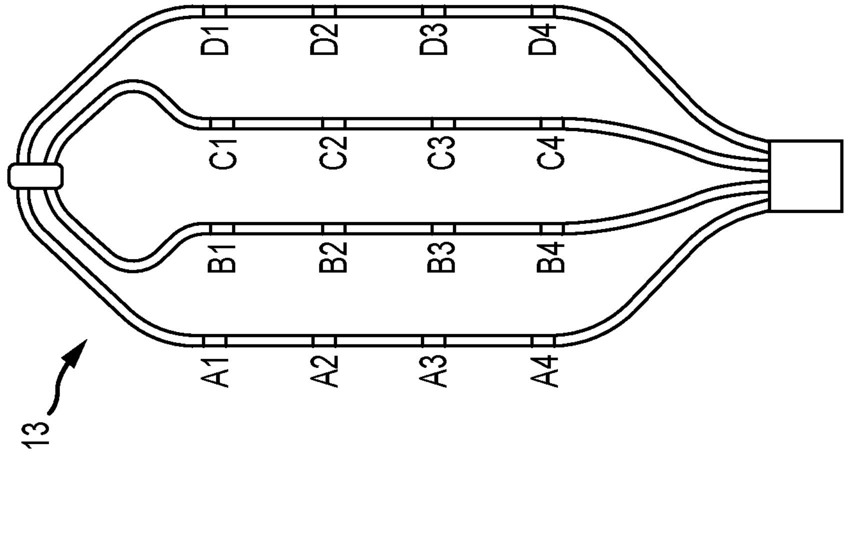

For ease of reference in this description, FIG. 3B provides alphanumeric labels for the along- and across-spline bipoles. FIG. 3B omits alphanumeric labels for the diagonal bipoles, but this is only for the sake of clarity in the illustration. It is expressly contemplated that the teachings herein can also be applied with respect to the diagonal bipoles.

Any bipole can, in turn, be used to generate a bipolar electrogram according to techniques that will be familiar to those of ordinary skill in the art. Moreover, these bipolar electrograms can be combined (e.g., linearly combined) to generate electrograms, again including activation timing information, in any direction of the plane of catheter 13 by computing an E-field loop for a clique of electrodes. United States patent application publication no. 2018/0296111 (the '111 publication), which is hereby incorporated by reference as though fully set forth herein, discloses details of computing an E-field loop for a clique of electrodes on a HD grid catheter. These electrograms are referred to herein as "omnipolar electrograms," and their corresponding directions are referred to herein as "omnipoles" or "virtual bipoles."

In any event, catheter 13 can be used to simultaneously collect a plurality of electrophysiology data points for the various bipoles defined by electrodes 17 thereon, with each such electrophysiology data point including both localization information (e.g., position and orientation of a selected bipole) and an electrogram signal for the selected bipole. For purposes of illustration, methods according to the instant disclosure will be described with reference to individual electrophysiology data points collected by catheter 13. It should be understood, however, that the teachings herein can be applied, in serial and/or in parallel, to multiple electrophysiology data points collected by catheter 13.

Catheter 13 (or multiple such catheters) are typically introduced into the heart and/or vasculature of the patient via one or more introducers and using familiar procedures. Indeed, various approaches to introduce catheter 13 into a patient's heart, such as transseptal approaches, will be familiar to those of ordinary skill in the art, and therefore need not be further described herein.

Since each electrode 17 lies within the patient, location data may be collected simultaneously for each electrode 17 by system 8. Similarly, each electrode 17 can be used to gather electrophysiological data from the cardiac surface (e.g., endocardial electrograms). The ordinarily skilled artisan will be familiar with various modalities for the acquisition and processing of electrophysiology data points (including, for example, both contact and non-contact electrophysiological mapping), such that further discussion thereof is not necessary to the understanding of the techniques disclosed herein. Likewise, various techniques familiar in the art can be used to generate a graphical representation of a cardiac geometry and/or of cardiac electrical activity from the plurality of electrophysiology data points. Moreover, insofar as the ordinarily skilled artisan will appreciate how to create electrophysiology maps from electrophysiology data points, the aspects thereof will only be described herein to the extent necessary to understand the present disclosure.

Returning now to FIG. 1, in some embodiments, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20 may comprise, for example, a conventional general-purpose computer, a special-purpose computer, a distributed computer, or any other type of computer. The computer 20 may comprise one or more processors 28, such as a single central processing unit ("CPU"), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17 placed in the heart 10 are exposed to the field from a current pulse and are measured with respect to ground, such as belly patch 21. In practice the catheters within the heart 10 may contain more or fewer electrodes than the sixteen shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which system 8 measures positions. Data sets from each of the surface electrodes, the internal electrodes, and the virtual electrodes may all be used to determine the location of the roving electrodes 17 within heart 10.

The measured voltages may be used by system 8 to determine the location in three-dimensional space of the electrodes inside the heart, such as roving electrodes 17 relative to a reference location, such as reference electrode 31. That is, the voltages measured at reference electrode 31 may be used to define the origin of a coordinate system, while the voltages measured at roving electrodes 17 may be used to express the location of roving electrodes 17 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described, for example, in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In aspects of the disclosure, system 8 can be a hybrid system that incorporates both impedance-based (e.g., as described above) and magnetic-based localization capabilities. Thus, for example, system 8 can also include a magnetic source 30, which is coupled to one or more magnetic field generators. In the interest of clarity, only two magnetic field generators 32 and 33 are depicted in FIG. 1, but it should be understood that additional magnetic field generators (e.g., a total of six magnetic field generators, defining three generally orthogonal axes analogous to those defined by patch electrodes 12, 14, 16, 18, 19, and 22) can be used without departing from the scope of the present teachings. Likewise, those of ordinary skill in the art will appreciate that, for purposes of localizing catheter 13 within the magnetic fields so generated, can include one or more magnetic localization sensors (e.g., coils).

In some embodiments, system 8 is the EnSite™ Velocity™ or EnSite Precision™ cardiac mapping and visualization system of Abbott Laboratories. Other localization systems, however, may be used in connection with the present teachings, including for example the RHYTHMIA HDX™ mapping system of Boston Scientific Corporation (Marlborough, Mass.), the CARTO navigation and location system of Biosense Webster, Inc. (Irvine, Calif.), the AURORA® system of Northern Digital Inc. (Waterloo, Ontario), Stereotaxis, Inc.'s NIOBE® Magnetic Navigation System (St. Louis, Mo.), as well as MediGuide™ Technology from Abbott Laboratories.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Aspects of the disclosure relate to generating electrophysiology maps, and in particular to mapping the electrical activation of tissue. Graphical representations of such electrophysiology maps can also be output, for example on display 23. System 8 can therefore include an activation mapping and visualization module 58.

Figure 4:
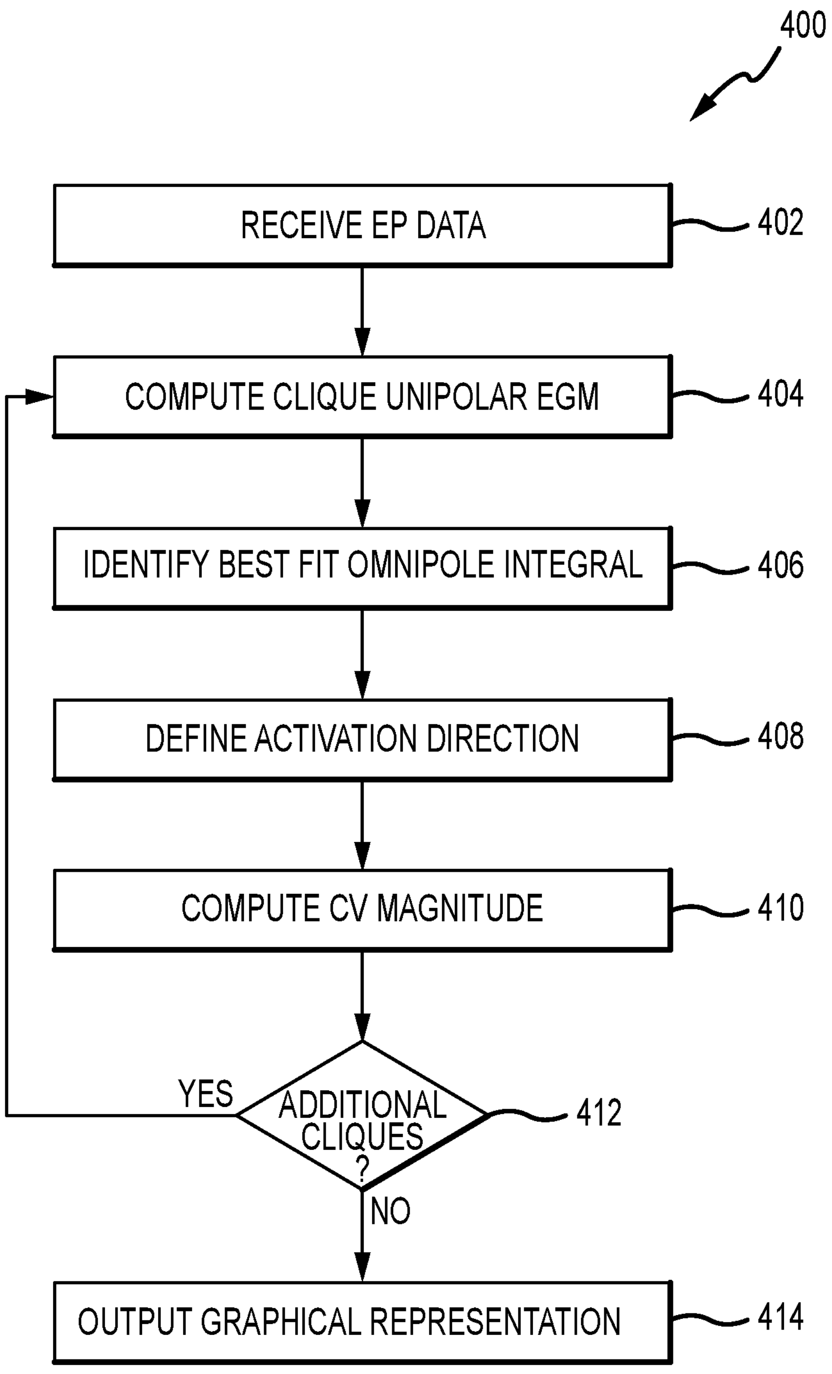
FIG. 4 is a flowchart of representative steps that can be carried out according to aspects of the instant disclosure.

One exemplary method according to aspects of the instant disclosure, which uses cardiac activation mapping as illustrative, will be explained with reference to the flowchart of representative steps presented as FIG. 4. In some embodiments, for example, flowchart 400 may represent several exemplary steps that can be carried out by electroanatomical mapping system 8 of FIG. 1 (e.g., by processor 28 and/or activation mapping and visualization module 58). It should be understood that the representative steps described below can be either hardware- or software-implemented. For the sake of explanation, the term "signal processor" is used herein to describe both hardware- and software-based implementations of the teachings herein.

In block 402, system 8 receives electrophysiological data measured by electrodes 17 on catheter 13. As discussed above, electrodes 17 define a plurality of electrode cliques, with each clique including three (or, in some embodiments of the disclosure, four or more) electrodes. For instance, aspects of the instant disclosure will be described with reference to the three-electrode clique made up of electrodes C2, C3, and D2.

Figure 5A:
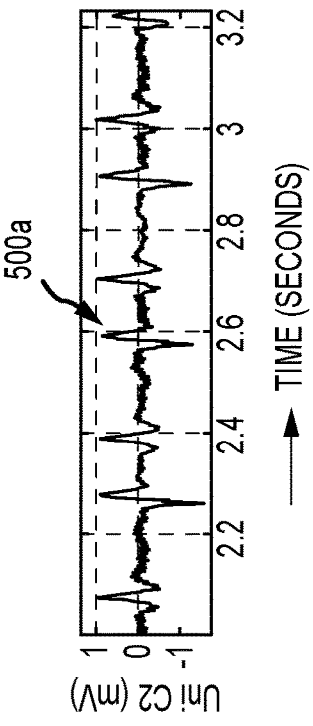
FIGS. 5A through 5C are representative unipolar electrograms for a three-electrode clique on a multi-electrode catheter, namely for the clique of electrodes C2, C3, and D2 according to the nomenclature of FIGS. 3A and 3B.
Figure 5B:
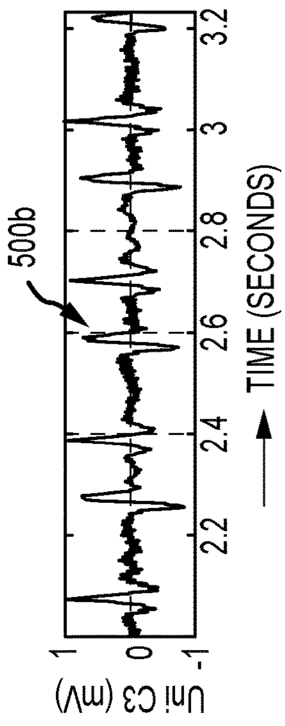
Figure 5C:
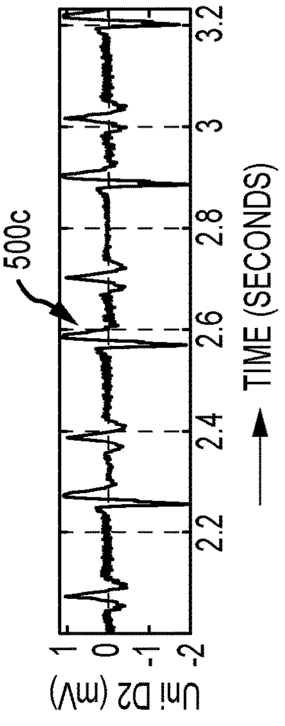

Those of ordinary skill in the art will recognize that each of electrodes C2, C3, and D2 can measure a unipolar electrogram (e.g., with respect to a belly patch). Exemplary unipolar electrograms 500*a*, 500*b*, and 500*c* for electrodes C2, C3, and D2 are shown in FIGS. 5A, 5B, and 5C, respectively.

Figure 6A:
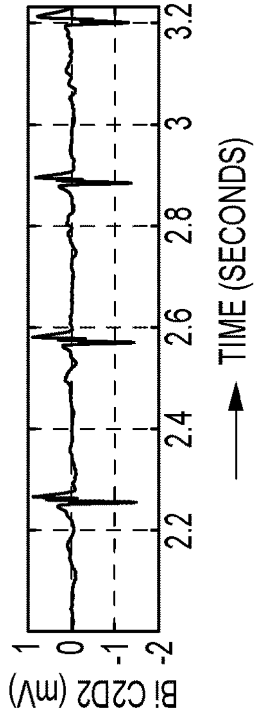
FIGS. 6A and 6B are orthogonal bipolar electrograms for the clique of electrodes C2, C3, and D2 according to the nomenclature of FIGS. 3A and 3B.
Figure 6B:
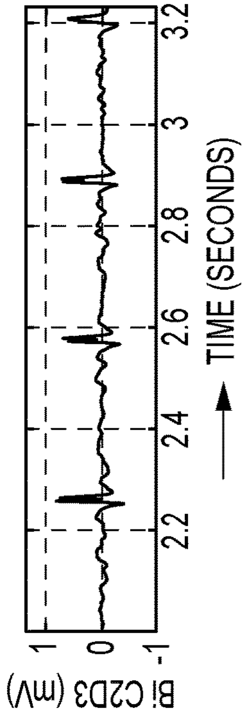

Further, electrodes C2, C3, and D2 define two orthogonal bipoles, namely C3-C2 along spline 210 and C2-D2 across splines 210, 208. Each bipole can measure a bipolar electrogram, as shown in FIG. 6A for bipole C2-D2 and in FIG. 6B for bipole C3-C2.

In block 404, system 8 determines a unipolar electrogram for the clique, denoted φ(t). In embodiments of the disclosure, φ(t) is an average of the unipolar electrograms for the clique (that is, an average of unipolar electrograms 500*a*, 500*b*, and 500*c*), though other representative unipolar electrograms are also contemplated. For instance, an initial average unipolar electrogram for the clique can be refined through temporal adjustments based on initial estimates of activation direction and conduction velocity magnitude for the clique.

Figure 7:
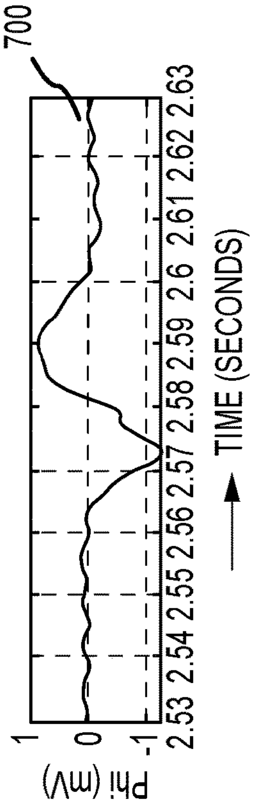
FIG. 7 is an average unipolar electrogram for the clique of electrodes C2, C3, and D2 according to the nomenclature of FIGS. 3A and 3B.

FIG. 7 illustrates an average unipolar electrogram 700 for clique of electrodes C2, C3, D2. As can be seen in FIG. 7, average unipolar electrogram 700 exhibits noise due, for example, to the AC power signal.

The teachings of the '111 application can be applied to clique of electrodes C2, C3, D2 as well to compute omnipolar electrograms for omnipoles (or "virtual bipoles") at any orientation within the plane of catheter 13 (note that bipole C2-D2 is oriented at 0 degrees, while bipole C3-C2 is oriented at 90 degrees). Using these teachings, in block 406, system 8 identifies the omnipole orientation where the integral of the corresponding omnipolar electrogram exhibits the best morphological match to the clique unipolar electrogram computed in block 404.

Figure 9A:
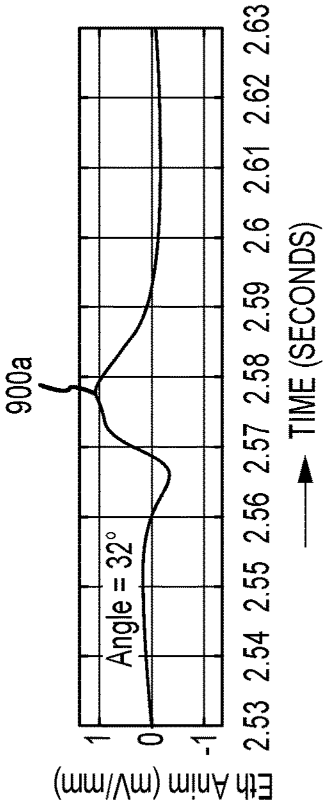
FIGS. 9A through 9C are, respectively, the integrals with respect to time of the omnipolar electrograms of FIGS. 8A through 8C.
Figure 9B:
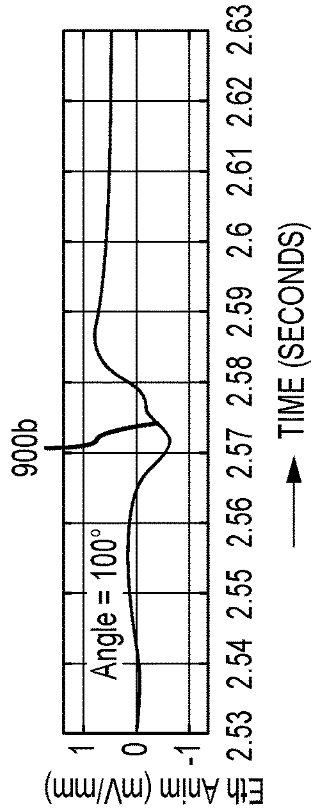
Figure 9C:
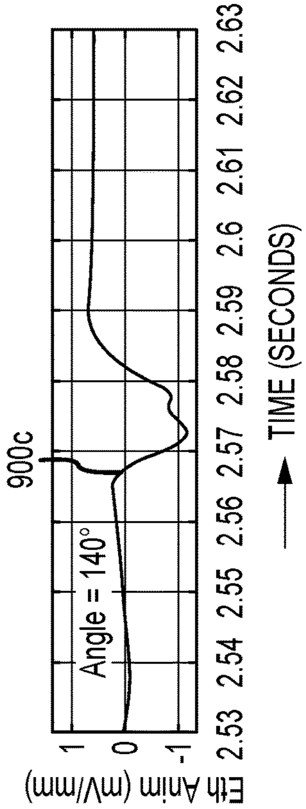
Figure 8A:
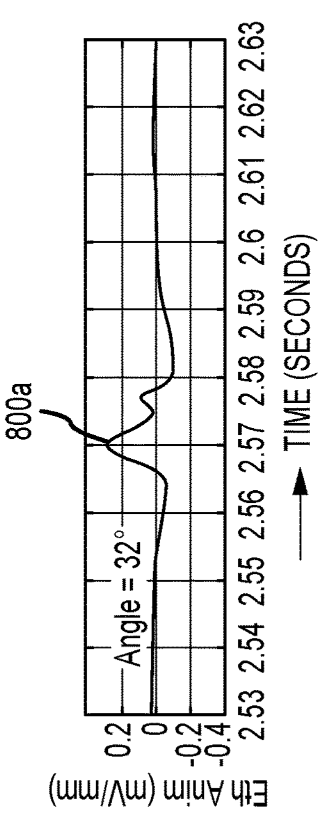
FIGS. 8A through 8C show omnipolar electrograms at 32 degrees, 100 degrees, and 140 degrees, respectively, for the clique of electrodes C2, C3, and D2 according to the nomenclature of FIGS. 3A and 3B.
Figure 8B:
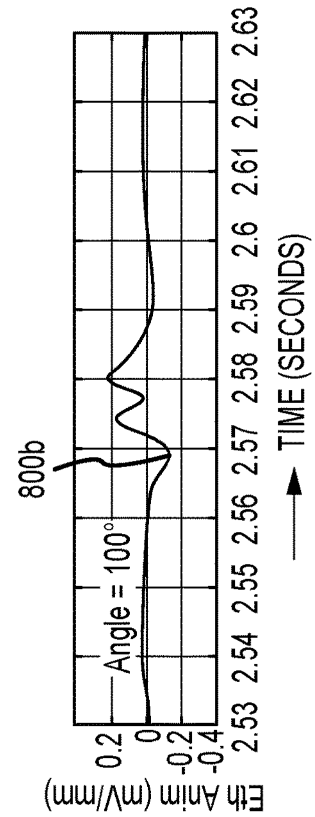
Figure 8C:
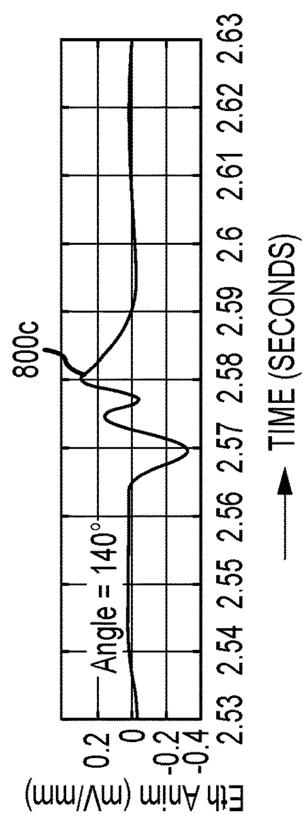

FIGS. 8A-8C and 9A-9C illustrate application of block 406. FIGS. 8A-8C depict omnipolar electrograms 800*a*, 800*b*, and 800*c* for omnipoles oriented at 32 degrees, 100 degrees, and 140 degrees, respectively. The corresponding integrals with respect to time 900*a*, 900*b*, and 900*c* are shown in FIGS. 9A-9C, respectively. Of course, similar electrograms and integrals could be computed for other omnipole orientations; those shown in FIGS. 8A-8C and 9A-9C are merely exemplary.

It should be understood that there are various approaches to computing the integrals of omnipolar electrograms. For instance, several omnipolar electrograms can be computed (e.g., according to the teachings of the '111 application), and then the integral of each omnipolar electrogram can be computed. This may require substantial computing resources, however, because each signal must be determined and then integrated independently. Thus, another approach is to compute an E-field loop (e.g., according to the teachings of the '111 application), integrate the E-field loop, and then project the integrated E-field loop in the various omnipole directions. The latter approach is more computationally efficient, because it requires a single integral (e.g., of the E-field loop) and multiple projections (e.g., of the integrated E-field loop in various omnipole orientations), as opposed to the former approach's multiple projections (e.g., of the E-field loop in the various omnipole orientations) and multiple integrals (e.g., of the various omnipolar electrograms).

In still other embodiments, the integrals of the omnipolar electrograms can be computed in reverse temporal order (e.g., with the limits of the integral expressed from right-to-left, rather than from left-to-right, with reference to FIGS. 8A-8C). It may, in fact, be desirable to compute both a forward integral and a reverse integral of an omnipolar electrogram, and then to combine the two integrals, such as using a smoothly time varying convex combination that progressively discounts the forward integral and progressively accentuates the reverse integral. This combined approach advantageously minimizes the impact of offset in the head or tail of an individual integral that results from propagating and accumulating offsets in the omnipolar electrograms being integrated.

Those of ordinary skill in the art will appreciate that a smoothly time varying convex combination can take various forms. For instance, the forward integral can be weighted by a time varying weight a(t), and the reverse integral can be weighted by a time varying weight b(t), where a(t)+b(t)=1 for any time t. According to some aspects of the disclosure, a(t) linearly increases from 0 to 1 and b(t) linearly decays from 1 to 0.

In any case, system 8 identifies the integral (e.g., 900*a*, 900*b*, 900*c*) that exhibits the best morphological match to φ(t) (e.g., 700). This integral is referred to herein as the "best-fit omnipole integral." Morphological matching techniques will be familiar to those of ordinary skill in the art and need not be further described herein. Applying such techniques, however, it can be recognized that, in the case of FIG. 7, on the one hand, and FIGS. 9A-9C, on the other hand, the best-fit omnipole integral is oriented at about 140 degrees, as shown in FIG. 9C.

In block 408, system 8 defines the orientation of the best-fit omnipole integral from block 406 as the activation direction for the clique. Thus, the activation direction for clique of electrodes C2, C3, D2 is about 140 degrees.

In block 410, system 8 computes the magnitude of the conduction velocity for the clique from the best-fit omnipole integral and the clique unipole φ(t). For instance, the conduction velocity magnitude can be computed as a ratio between the amplitude of the clique unipole φ(t) and the amplitude of the best-fit omnipole integral (that is, along the defined activation direction for the clique of electrodes).

Figure 10:
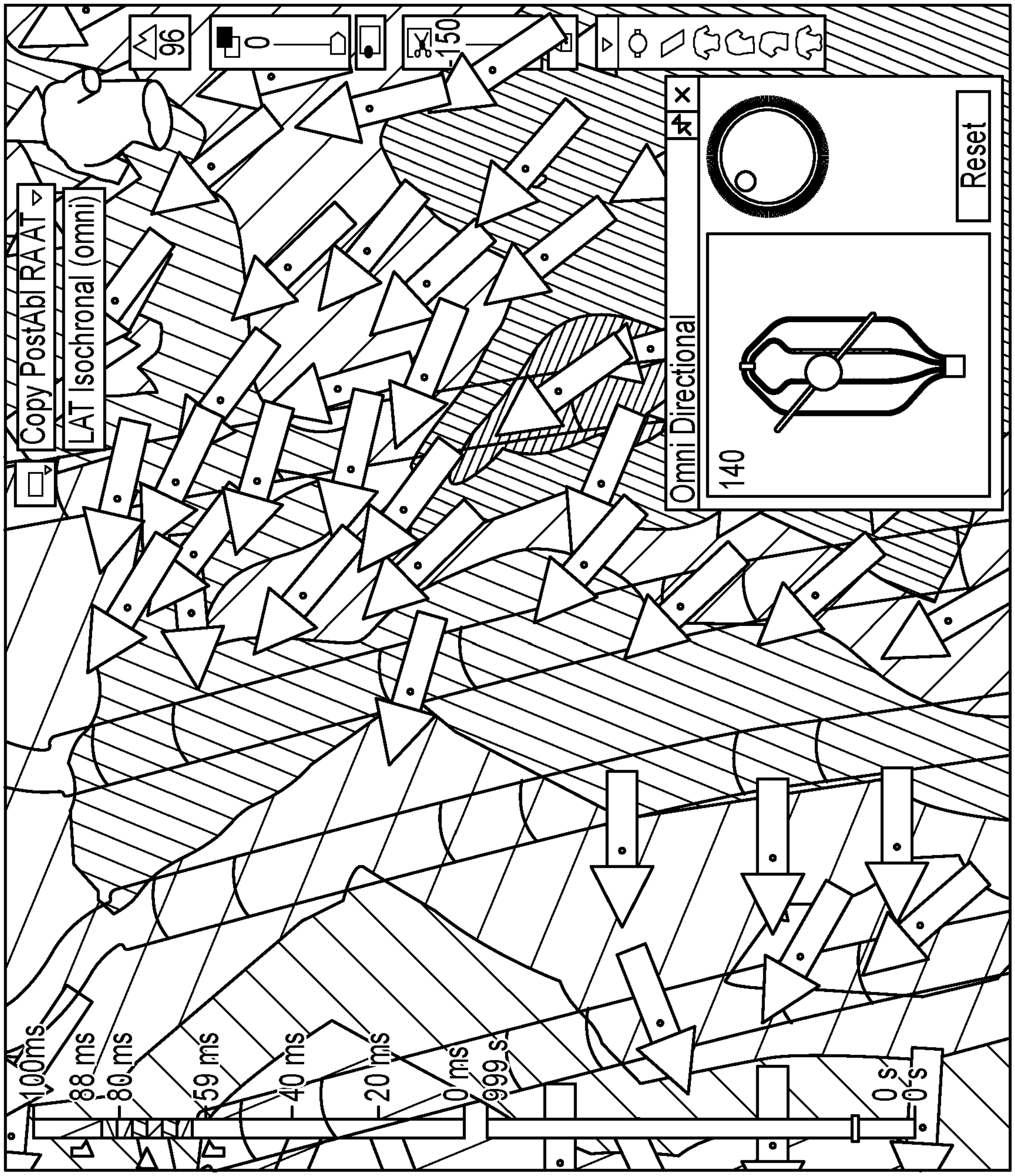
FIG. 10 is a representative visualization of an activation map according to aspects of the instant disclosure.

Decision block 412 considers whether there are additional cliques to analyze. If so, the process repeats from block 404. If not, a graphical representation of the activation map, such as 1000 in FIG. 10, can be output in block 414.

Although several embodiments have been described above with a certain degree of particularity, those skilled in the art could make numerous alterations to the disclosed embodiments without departing from the spirit or scope of this invention.

For example, the teachings herein can be applied in real time (e.g., during an electrophysiology study) or during post-processing (e.g., to electrophysiology data points collected during an electrophysiology study performed at an earlier time).

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of mapping cardiac activation, comprising:

receiving, at an electroanatomical mapping system, electrophysiological data from a plurality of electrodes carried by a multi-electrode catheter, the plurality of electrodes defining a plurality of cliques; and for each clique of the plurality of cliques, the electroanatomical mapping system executing a process comprising:

identifying an integral of an omnipolar electrogram for the clique having a best morphological match to a unipolar electrogram for the clique;

defining an orientation of the omnipolar electrogram for the clique having the best morphological match to the unipolar electrogram for the clique as an activation direction for the clique; and computing a conduction velocity magnitude for the clique using the integral of the omnipolar electrogram for the clique and the unipolar electrogram for the clique, thereby determining a cardiac activation map.

2. The method according to claim 1, wherein the unipolar electrogram for the clique comprises a representative unipolar electrogram for the clique.

3. The method according to claim 2, wherein the representative unipolar electrogram comprises an average unipolar electrogram for the clique.

4. The method according to claim 1, wherein computing a conduction velocity magnitude for the clique using the integral of the omnipolar electrogram for the clique and the unipolar electrogram for the clique comprises computing the conduction velocity magnitude for the clique as a ratio of an amplitude of the unipolar electrogram for the clique to an amplitude of the integral of the omnipolar electrogram along the activation direction for the clique.

5. The method according to claim 1, wherein the integral of the omnipolar electrogram for the clique comprises an integral of the omnipolar electrogram for the clique with respect to time.

6. The method according to claim 1, further comprising outputting a graphical representation of the cardiac activation map.

7. The method according to claim 1, wherein the multi-electrode catheter comprises a high density grid catheter.

8. The method according to claim 1, wherein each clique of the plurality of cliques comprises three electrodes that define two orthogonal bipoles.

9. An electroanatomical mapping system for generating a cardiac activation map, comprising:

an activation mapping and visualization processor configured to:

receive electrophysiological data from a plurality of electrodes carried by a multi-electrode catheter, the plurality of electrodes defining a plurality of cliques; and for each clique of the plurality of cliques, determine an activation direction and conduction velocity magnitude according to a process comprising:

identifying an integral of an omnipolar electrogram for the clique having a best morphological match to a unipolar electrogram for the clique;

defining an orientation of the omnipolar electrogram for the clique having the best morphological match to the unipolar electrogram for the clique as an activation direction for the clique; and computing a conduction velocity magnitude for the clique using the integral of the omnipolar electrogram for the clique and the unipolar electrogram for the clique, thereby determining a cardiac activation map.

10. The electroanatomical mapping system according to claim 9, wherein the activation mapping and visualization processor is further configured to output a graphical representation of the activation map.

11. The electroanatomical mapping system according to claim 9, wherein the unipolar electrogram for the clique comprises a representative unipolar electrogram for the clique.

12. The electroanatomical mapping system according to claim 11, wherein the representative unipolar electrogram for the clique comprises an average unipolar electrogram for the clique.

13. The electroanatomical mapping system according to claim 9, wherein computing a conduction velocity magnitude for the clique using the integral of the omnipolar electrogram for the clique and the unipolar electrogram for the clique comprises computing the conduction velocity magnitude for the clique as a ratio of an amplitude of the unipolar electrogram for the clique to an amplitude of the integral of the omnipolar electrogram for the clique.

14. The electroanatomical mapping system according to claim 9, wherein the integral of the omnipolar electrogram for the clique comprises an integral of the omnipolar electrogram for the clique with respect to time.

15. A method of mapping electrical activation of tissue, comprising:

receiving, at an electroanatomical mapping system, electrophysiological data from a plurality of electrodes carried by a high density grid catheter, the plurality of electrodes defining a plurality of cliques, each clique including three electrodes that define a pair of orthogonal bipoles; and for each clique of the plurality of cliques, the electroanatomical mapping system executing a process comprising:

identifying an integral of an omnipolar electrogram for the clique having a best morphological match to a unipolar electrogram for the clique;

defining an orientation of the omnipolar electrogram for the clique having the best morphological match to the unipolar electrogram for the clique as an activation direction for the clique; and computing a conduction velocity magnitude for the clique using the integral of the omnipolar electrogram for the clique and the unipolar electrogram for the clique, thereby determining an activation map for the tissue.

16. The method according to claim 15, wherein the unipolar electrogram for the clique comprises a representative unipolar electrogram for the clique.

17. The method according to claim 16, wherein the representative unipolar electrogram comprises an average unipolar electrogram for the clique.

18. The method according to claim 15, wherein computing a conduction velocity magnitude for the clique using the integral of the omnipolar electrogram for the clique and the unipolar electrogram for the clique comprises computing the conduction velocity magnitude for the clique as a ratio of an amplitude of the unipolar electrogram for the clique to an amplitude of the integral of the omnipolar electrogram for the clique.

19. The method according to claim 15, wherein the integral of the omnipolar electrogram for the clique comprises an integral of the omnipolar electrogram for the clique with respect to time.

20. The method according to claim 15, further comprising outputting a graphical representation of the activation map for the tissue.

* * * * *